United States Patent [19]

Genco et al.

[11] 4,310,242

[45] Jan. 12, 1982

[54] FIELD TEST UNIT FOR WINDSCREEN OPTICAL EVALUATION

[75] Inventors: Louis V. Genco, Enon; Harry L. Task, Montgomery County, both of Ohio

[73] Assignee: The United States of America as represented by the Secretary of the Air Force, Washington, D.C.

[21] Appl. No.: 136,210

[22] Filed: Apr. 1, 1980

[51] Int. Cl.³ .............................................. G01N 21/41
[52] U.S. Cl. .................................... 356/128; 356/239; 356/365
[58] Field of Search ................... 356/32, 33, 365, 121, 356/124, 124.5, 128, 239

[56] References Cited

U.S. PATENT DOCUMENTS

| 2,871,756 | 2/1959 | Graves et al. | 356/239 |
|---|---|---|---|
| 3,373,652 | 3/1968 | Flader | 356/33 |
| 3,578,869 | 5/1971 | Irland et al. | 356/239 |
| 3,811,775 | 5/1974 | Abu-Saud | 356/239 |

OTHER PUBLICATIONS

Consortini et al., "Investigation of Atmospheric Turbulence by Narrow Laser Beams", Applied Optics, vol. 9, No. 11, (Nov. 1970), pp. 2543-2547.

*Primary Examiner*—R. A. Rosenberger
*Attorney, Agent, or Firm*—Donald J. Singer; Casimer K. Salys

[57] ABSTRACT

An apparatus for analyzing the deleterious characteristics of optically transparent bodies, including distortion, multiple imaging and birefringence. A beam of light is projected along an optical axis onto a beam splitter. The reflected segment passes through the transparent body and is then reflected back along nearly the same path toward the beam splitter by a retro-reflective screen lying at the image plane of the beam. The portion of the reflected beam passing directly through the beam splitter is detected by an optical sensor in substantial orientation with the axis of the beam reaching it. Distortions and multiple imaging are detected by shape changes and images, respectively, in a pattern of opaque areas superimposed on the originating beam. Birefringence is analyzed by polarizing the originating beam and observing the color pattern and intensity reaching the sensor.

6 Claims, 8 Drawing Figures

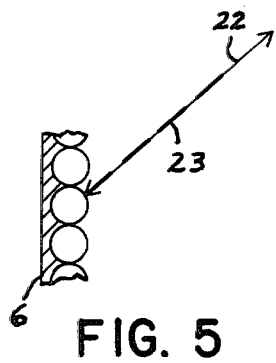
FIG. 5
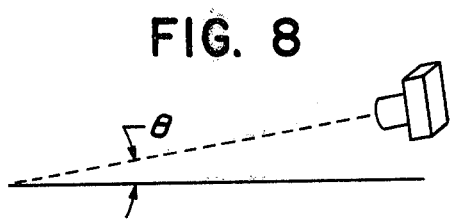
FIG. 8
FIG. 3
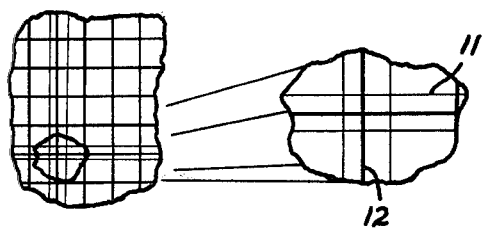
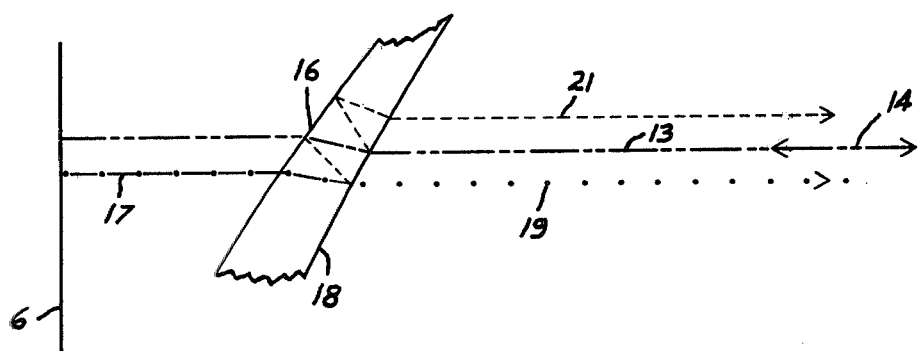
FIG. 4

FIELD TEST UNIT FOR WINDSCREEN OPTICAL EVALUATION

RIGHTS OF THE GOVERNMENT

The invention described herein may be manufactured and used by or for the Government of the United States for all governmental purposes without the payment of any royalty.

BRIEF SUMMARY

The invention is directed to an optical apparatus, used to analyze the deleterious optical effects of a windscreen or other transparent body when it is inserted into the path of observation. Optical distortion is measured by noting its effect on a precision pattern projected through the transparent body. The multiple imaging phenomenon appears in the same projected pattern and is generally characterized by asymmetrically distributed images of the fundamental pattern. By polarizing an unpatterned beam of light, and projecting it through the same transparent body, the optical sensor in the apparatus records the birefringence characteristics of the body.

To analyze distortion and multiple imaging a beam of light, with the pattern of interest superimposed, is projected through the transparent body to a focus on a retro-reflective screen. A segment of the returning beam is redirected after it again passes through the transparent body, with the new direction being substantially aligned to the axis of an optical sensor. Pattern images and variations in the pattern shape correspond directly to the characteristics of the transparent body.

Birefringence is analyzed by polarizing the light beam prior to its first pass through the transparent body. No pattern is necessary. The retro-reflected beam reaching the optical sensor contains a spatial distribution of color corresponding to the birefringence characteristics of the transparent body. The color hue is further accentuated by inserting a linear polarizer into the path of the beam at a point immediately preceeding the optical sensor.

DESCRIPTION OF THE DRAWINGS

FIG. 3 shows a segment of the image reaching the optical sensor, with particular interest to the multiple imaging effects.

FIG. 4 schematically shows various ray paths contributing to the multiple imaging effect.

FIG. 5 is a cross-sectional schematic of one retro-reflective screen design.

FIG. 8 schematically depicts misorientation between the sensor axis and the incident beam axis.

DETAILED DESCRIPTION

Figure 1:
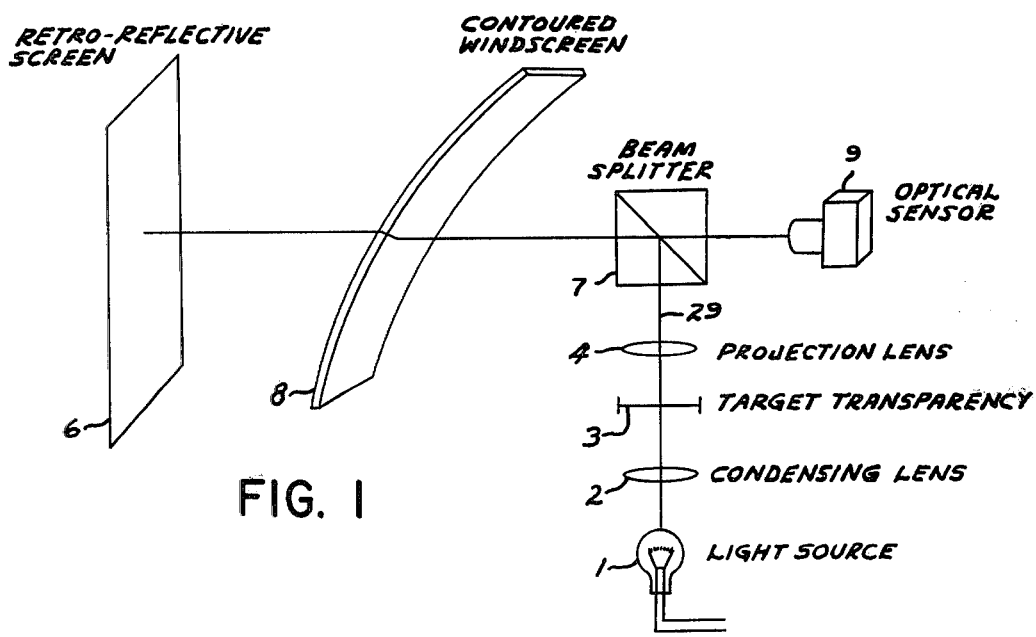
FIG. 1 schematically depicts an embodiment used to analyze distortion and multiple imaging.

Optically transparent, asymmetrically contoured bodies have, as a general rule, been difficult to quantitatively evaluate and compare on the basis of their optical characteristics. A prime example of a structural element in which optical quality is critical, yet difficult to quantitatively compare, is the laminated canopy or windscreen of aircraft.

The invention pertains to a test instrument apparatus which evaluates a variety of optical characteristics. In particular, the characteristics are those of central concern when dealing with asymmetrically contoured transparent bodies. As embodied, the apparatus provides a measure of the optical distortion, including its spatial distribution, the multiple imaging characteristics, and the inherent birefringence of the optical element being evaluated. Furthermore, upon appropriate calibration the apparatus is readily amenable to quantization, for relative comparison and establishment of acceptance thresholds. No less valuable is the compact size of the apparatus, allowing on-site evaluation. Heretofore, equipment capable of performing comparable windscreen evaluations required specially instrumented, room size, test facilities.

Identical reference numerals designate like elements throughout the various embodiments depicted in the drawings.

Attention is now directed to FIG. 1, in which one embodiment of the invention is schematically depicted. The configuration in FIG. 1 evaluates distortion by projecting an accurately patterned beam of luminous energy through the contoured body and detecting the pattern distortion upon reflection from a retro-reflective screen. As depicted in the figure, light originating in broad spectrum luminous energy source 1 is condensed into a beam by lens 2 and projected through an interchangeable target transparency, 3. The beam composition is altered into a pattern by opaque areas in the target. The succeeding element, projection lens 4, focuses an image of the pattern on planar retro-reflective screen 6, after a portion is deflected by beam splitter 7 and passes through contoured windscreen 8. A lesser portion of the patterned image reflected from screen 6, containing distortion introduced by windscreen 8, passes on its return off retro-reflective screen 6 through beam splitter 7 toward optical sensor 9. Though sensor 9 could be any one of many video detection devices, permanence and accuracy suggest a precision camera.

Figure 2:
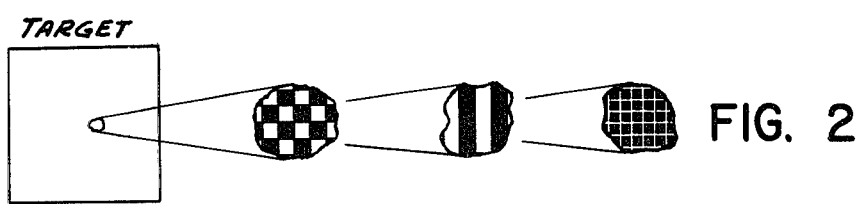
FIG. 2 schematically depicts typical target patterns.

Once the distortion is photographically recorded its distribution and amplitude may be quantified in any one of many conventional manners. FIG. 2 depicts typical examples of patterns used in distortion analysis. Distortion is readily perceived as a loss in pattern symmetry and linearity.

The apparatus in FIG. 1 inherently contains the ability to detect another optical defect encountered in windscreens, conventionally known as multiple imaging. Looking at the grid pattern in FIG. 3, presumed to be the negative of a photograph taken with sensor 9, one notes the presence of shadow-like grids 11, having a lesser intensity than fundamental grid 12. They are created by unwanted reflections at the exterior surfaces of windscreen 8, in a manner similar to that generally depicted in the schematic of FIG. 4.

The paths of the dominant reflections are depicted in FIG. 4. In that figure, heavy and long dashed lines 13 represent the incident light ray, while heavy but short dashed lines 14 represent its direct return from retro-reflective screen 6. Reflections of incident ray 13 from external surface 16, represented by dashes 17, are also reflected from external surface 18 in the direction of screen 6. The return ray, shown by dots 19, creates a ghost image at optical sensor 9. An antisymmetric ghost image to that of ray 19 is created by reflections of retro-reflected ray 14 on its passage through surface 18. The portion so reflected bounces off surface 16 and is then directed along dashed line 21. Though present, the low intensities of other multiple images seldom affect windscreen performance sufficiently to justify detailed analysis. The two described above are, however, measurable defects, and thus serve as indices of the multiple imaging created by the windscreen.

The optical characteristics of retro-reflective screen 6 are important in the operation of the composite apparatus. Fundamentally, the apparatus requires that any ray reflected from the screen must nearly retrace the path of the incident ray. For instance, the reflected ray represented by light solid line 22 in FIG. 5, originates an incident ray 23. This figure depicts a commercially available form of retro-reflective screen made from a layer of glass micro-spheres coated on the reverse side with aluminum, manufactured by 3M Corporation and sold under the registered trademark Scotchlight. Although incident and reflected rays 23, 22 are depicted in FIG. 5 as traveling along a generally common line, it should be understood that their actual paths are believed to be substantially parallel but separated or displaced from one another by an extremely small distance. In such manner the reflected ray 22 passes through a slightly different portion of the windscreen 8 than that traveled by the incident ray 23. Therefore, the effects of windscreen distortion on the incident ray 23 are not reversed and thus canceled out in the reflected ray 22.

The general configuration of the apparatus described above for measuring distortion and multiple imaging is readily capable of measuring birefringence effects when supplemented with linear polarizers. Birefringence, as an optical phenomenon, appears as a rainbow of colors dispersed in patterns over the surface of the optically transparent body when viewing through it. The aircraft windscreen, to which the embodying test apparatus is directed, exhibits this phenomenon at high altitude, where the highly polarized sun light interacts with the Brewster's angle orientation of the windscreen, and variations in refractive indices, to alter the light's color composition. Undoubtedly, the presence of these birefringence color patterns degrades the visibility through the windshield, and as such, defines a characteristic of the windscreen which must be evaluated. Furthermore, birefringence effects are variable, changing in pattern, color and amplitude as a function of time and orientation.

Figure 6:
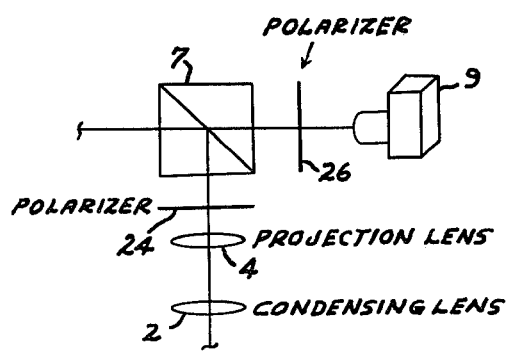
FIG. 6 schematically depicts the embodiment used to measure birefringence effects.

The invention encompasses a variant to the embodiment depicted in FIG. 1 by which birefringence characteristic can be ascertained. The pertinent elements distinguishing this embodiment are schematically presented in FIG. 6. Target transparency 3 is no longer present. Linear polarizers 24 and 26 are shown in the optical paths from the light source 1 and in the direction of optical sensor 9, respectively. The birefringence effects on the polarized light projected through the windscreen are accentuated by introducing polarizer 26, obtaining birefringence effects that are more distinguishable by increasing color saturation.

Figure 7:
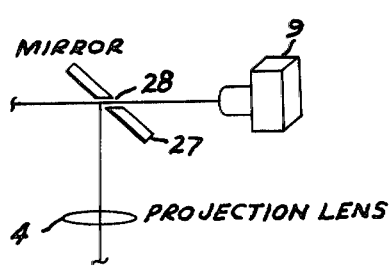
FIG. 7 contains the schematic of a functional alternate for the beam splitter.

Another embodiment of the invention, pertaining to configurations seeking measures of distortion, multiple imaging or birefringence, appears schematically in FIG. 7. In this case, beam splitter 7 has been replaced with a canted mirror, 27, having a passage, 28, therethrough. Passage 28 is preferably coated with nonreflective material and is aligned with optical sensor 9. Undoubtedly, sensor 9 is optically corrected and physically situated in close proximity to mirror 27, so that the full image of the target pattern or polarized light beam focused on screen 6 can be observed. The effects of the passage on the image formed at screen 6 are minuscule because the incident light beam reflected off mirror 27 is substantially defocused at the mirror plane.

With an understanding of the fundamental invention at hand, attention is now directed to a design parameter which demands consideration if the invention is to be utilized in undertaking quantitative analysis of distortion or birefringence. A strict theoretical analysis of the apparatus depicted in FIG. 1, presupposing that the optical axes of the projection toward screen 6, the return from screen 6 and optical sensor 9 are in perfect alignment, will conclude that distortion and bifringence effects are not discernible at sensor 9. The practical world, however, produces a different result which is caused by a nominal misorientation of the sensor axis from the optical axis in the direction of the screen. This design characteristic is depicted, with significant exaggeration, in FIG. 8. The import of this design consideration lies in the recognition that sensor orientation affects the distortion and birefringence characteristics, and further that the parameter must be controlled if quantitative analysis is to occur.

The invention has been shown and described with reference to various embodiments. The scope and spirit of the combination by which fundamental concepts underlying the invention are joined encompass a significantly broader range of embodiments.

Their existence is fully contemplated by the inventors in claiming:

1. An apparatus for measuring the optical characteristics of a transparent body, comprising:
   means for generating and projecting a beam of light along a first optical axis;
   means for redirecting onto a second optical axis a portion of the light beam projected along the first optical axis, said means located between said generating and projecting means and the transparent body;
   a planar retro-reflective screen positioned orthogonal to and intersecting the second optical axis at an image plane of the projected light beam portion after it has been redirected by said redirecting means and has passed through the transparent body; and
   an optical sensor positioned in substantial alignment with the second optical axis for sensing and recording an image of the light beam portion after it has been reflected from the retro-reflective screen and has passed back through the transparent body and redirecting means along the second optical axis to said optical sensor.

2. The apparatus recited in claim 1, further including means for creating contrast patterns in the generated beam of light.

3. The apparatus recited in claim 2, wherein said means for redirecting comprises a beam splitter and said means for creating contrast patterns comprises a transparency having a pattern of opaque regions.

4. The apparatus recited in claim 2, wherein said means for redirecting comprises a mirror having a passage therethrough aligned with the second optical axis.

5. The apparatus recited in claim 1, further including means for polarizing the generated beam of light.

6. The apparatus recited in claim 5, wherein said means for redirecting comprises a beam splitter and wherein the apparatus further contains a linear polarizer on the second optical axis between the beam splitter and the optical sensor.

* * * * *